(12) United States Patent
Trask (10) Patent No.: US 8,926,596 B2
(45) Date of Patent: Jan. 6, 2015

(54) LOADING A TISSUE CLOSURE DEVICE ONTO A DELIVERY DEVICE

(75) Inventor: David Trask, Redwood City, CA (US)

(73) Assignee: Abbott Laboratories, Abbott Park, IL (US)

( * ) Notice: Subject to any disclaimer, the term of this patent is extended or adjusted under 35 U.S.C. 154(b) by 2239 days.

(21) Appl. No.: 11/750,796

(22) Filed: May 18, 2007

(65) Prior Publication Data

US 2008/0287923 A1    Nov. 20, 2008

(51) Int. Cl.
  *B23B 31/12* (2006.01)
  *A61B 17/10* (2006.01)
  *A61B 17/064* (2006.01)
  *A61B 17/068* (2006.01)
  *A61B 17/08* (2006.01)
  *A61B 17/00* (2006.01)

(52) U.S. Cl.
  CPC ............... *A61B 17/10* (2013.01); *A61B 17/064* (2013.01); *A61B 17/068* (2013.01); *A61B 17/083* (2013.01); *A61B 17/0057* (2013.01); *A61B 2017/00526* (2013.01); *A61B 2017/00668* (2013.01); *A61B 2017/00867* (2013.01)
  USPC .......................................................... 606/1

(58) Field of Classification Search
  USPC .................................................. 606/1, 41–52
  See application file for complete search history.

(56) References Cited

U.S. PATENT DOCUMENTS 6,277,117 B1 * 8/2001 Tetzlaff et al. .................. 606/48
2014/0039525 A1   2/2014 Trask

* cited by examiner

*Primary Examiner* — Aaron Roane
(74) *Attorney, Agent, or Firm* — Workman Nydegger; Randy Shen (57) ABSTRACT

A compression tool is configured to compress one or more components of a delivery device, such as a closure element and one or more flanges of a pusher tube. The compression tool includes clamping means configured to close or release with rotation of actuating means (e.g., rotating means). In a closed position, the clamping means can sufficiently compress the one or more components of the delivery device so that a technician can easily position a garage tube about the compressed delivery device components. The assembled delivery device (or assembled garage tube) can then be removed from the compression tool upon reverse rotation of the actuating means, and subsequent opening of the clamping means.

18 Claims, 8 Drawing Sheets

LOADING A TISSUE CLOSURE DEVICE ONTO A DELIVERY DEVICE

BACKGROUND OF THE INVENTION

1. The Field of the Invention

The present invention relates to systems, methods, and apparatus for compressing or mounting a closure element for insertion within a medical delivery device.

2. Background and Relevant Art

Catheterization and interventional procedures, such as angioplasty or stenting, are generally performed by inserting a hollow needle through a patient's skin and tissue into the vascular system. A guidewire may be advanced through the needle and into the patient's blood vessel accessed by the needle. The needle is then removed, enabling an introducer sheath to be advanced over the guidewire into the vessel, e.g., in conjunction with, or subsequent to, a dilator. A catheter—or other similar device—may then be advanced through a lumen of the introducer sheath, and over the guidewire, into a position for performing a medical procedure. Thus, the introducer sheath may facilitate introducing various devices into the vessel, while minimizing trauma to the vessel wall, and/or minimizing blood loss during a procedure.

Upon completing the procedure, the operator will remove the devices and introducer sheath, leaving a puncture site in the vessel wall. The operator, such as a nurse or physician, may then apply external pressure to the puncture site until clotting and wound sealing occur. Unfortunately, this may be time consuming for both the patient and the operator, and hence expensive. For example, the procedure may require as much as an hour of a physician's or nurse's time. Furthermore, the patient will usually need to remain bedridden for a substantial period of time after clotting to ensure closure of the wound. This procedure can be uncomfortable for the patient, and generally requires that the patient remain immobilized in the operating room, catheter lab, or holding area. In addition, a risk of hematoma exists from bleeding before hemostasis occurs.

Recent apparatus developed to aid hemostasis of the puncture site include devices configured to insert a flexible closure element about a puncture site, directly on the tissue. One such flexible closure element comprises a clip made of one or more memory materials or alloys, such as NITINOL (nickel titanium alloy) wire. In operation, a user, such as nurse or physician operator, handles a delivery device to deposit the closure element directly on the tissue, where the clip surrounds the puncture site. When the user releases the closure device, the clip (i.e., closure element) releases directly onto the tissue, and relaxes into a closed conformation. The clip also latches onto the tissue surrounding the puncture site, and squeezes the puncture site together. Accordingly, and due to its relative ease of use as well as reliability, a closure element—and corresponding delivery device—such as this can provide a number of advantages over conventional suturing mechanisms.

Mounting the closure element to the delivery device, however, can be difficult. For example, a conventional closure element, or clip, comprises a flexible, circular element that can be folded into a substantially cylindrical, tensioned state. The closure element can also be threaded over a cylindrical carrier tube, which is at least partially flared at the delivery end. An at least partially-hollow pusher tube may then be inserted over the carrier tube, and positioned adjacent the tensioned closure element that is in a tensioned, cylindrical configuration. In addition, the pusher tube generally includes a plurality of flanges or fingers that are at least partially flared away from the major vertical axis defined by the carrier tube, where the flaring aids contact with the closure element. A technician then inserts an assembly of the carrier tube, closure element, and pusher tube, in turn, within a garage tube that is configured with sufficient diameter to receive each of the items together. The pusher tube flanges and the closure element can be sufficiently compressed or tensioned toward the major axis defined by the carrier tube.

Compressing the pusher tube flanges and compressed/tensioned closure element against the major axis of the carrier tube, however, can be difficult, and time consuming. Conventional methods for tensioning this assembly of parts generally include hand assembly and subsequent hand compression thereof, and then manually pushing the components into the garage tube.

BRIEF SUMMARY OF THE INVENTION

Implementations of the present invention solve one or more problems in the art with systems, methods, and apparatus configured to compress one or more components of a delivery device together for efficient assembly and delivery of a closure element. In particular, apparatus in accordance with at least one implementation of the present invention include a compression tool having a plurality of clamps linked and actuated via a cam-operated ring. The ring is configured so that rotation thereof closes the plurality of clamps together about a closure element, and about the flanges of a pusher tube when assembled about a carrier tube. Once the pusher tube flanges and closure element are sufficiently compressed, a garage tube can be inserted about the pusher tube flanges and closure element to complete the assembly.

For example, a compression tool configured in accordance with at least one implementation of the present invention can include a base configured with receiving means. In one implementation, the receiving means are configured in size and shape to receive an unassembled portion of a delivery device on one side, and on another side, a preliminary assembly of components to be inserted. The compression tool can also include a clamping means positioned about the receiving means, where the clamping means is configured to move toward or away from the receiving means. In addition, the compression tool can include actuation means configured to, upon application of force in one direction, move the clamping means toward the receiving means, and upon application of force in an opposite direction, move the clamping means away from the receiving means.

Similarly, a compression tool system configured in accordance with an implementation of the present invention to compress a closure element can include a base having a support surface. The compression tool system can also include a plurality of blocks mounted radially about a hollow region formed in a center point of the support surface, as well as at least one clamp slidably positioned on each of the plurality of blocks. In addition, the compression tool can include at least one cam element fixedly mounted to each at least one clamp. Furthermore, the compression tool can include a rotating member rotatably mounted about the support surface. In at least one implementation, rotation of the rotating member in a clockwise or counterclockwise direction causes each at least one clamp to slide in a radially forward or reverse direction with respect to the rotating member.

By contrast, a method of compressing one or more components using a compression tool in accordance with an implementation of the present invention can involve preparing a preliminary assembly. In one implementation, the preliminary assembly includes at least a tensioned closure element positioned about a carrier tube. The method can also involve positioning the preliminary assembly adjacent a first side of a receiving means of a compression tool. In addition, the method can involve rotating an actuating means portion of the compression tool in a first direction. In at least one implementation, the actuating means engages a plurality of clamps in a radial direction toward the receiving means, such that the plurality of clamps compresses the preliminary assembly.

Additional features and advantages of exemplary implementations of the invention will be set forth in the description which follows, and in part will be obvious from the description, or may be learned by the practice of such exemplary implementations. The features and advantages of such implementations may be realized and obtained by means of the instruments and combinations particularly pointed out in the appended claims. These and other features will become more fully apparent from the following description and appended claims, or may be learned by the practice of such exemplary implementations as set forth hereinafter.

BRIEF DESCRIPTION OF THE DRAWINGS

In order to describe the manner in which the above-recited and other advantages and features of the invention can be obtained, a more particular description of the invention briefly described above will be rendered by reference to specific embodiments thereof which are illustrated in the appended drawings. Understanding that these drawings depict only typical embodiments of the invention and are not therefore to be considered to be limiting of its scope, the invention will be described and explained with additional specificity and detail through the use of the accompanying drawings in which.

DETAILED DESCRIPTION

The present invention extends to systems, methods, and apparatus configured to compress one or more components of a delivery device together for efficient assembly and delivery of a closure element. In particular, apparatus in accordance with at least one implementation of the present invention include a compression tool having a plurality of clamps linked and actuated via a cam-operated ring. The ring is configured so that rotation thereof closes the plurality of clamps together about a closure element, and about the flanges of a pusher tube when assembled about a carrier tube. Once the pusher tube flanges and closure element are sufficiently compressed, a garage tube can be inserted about the pusher tube flanges and closure element to complete the assembly.

Accordingly, and as will be appreciated more fully herein, implementations of the present invention can enable quick and efficient assembly of a device in which multiple components are inserted, such as a closure element used in a medical environment. Of course, one will appreciate from the following specification and claims that the apparatus and components disclosed herein can be practiced in a wide range of environments and settings where compression of one or more components for insertion into a device is desired. Nevertheless, for purposes of convenience in illustration, the present specification and claims are directed primarily to medical delivery devices and closure elements.

Figure 1A:
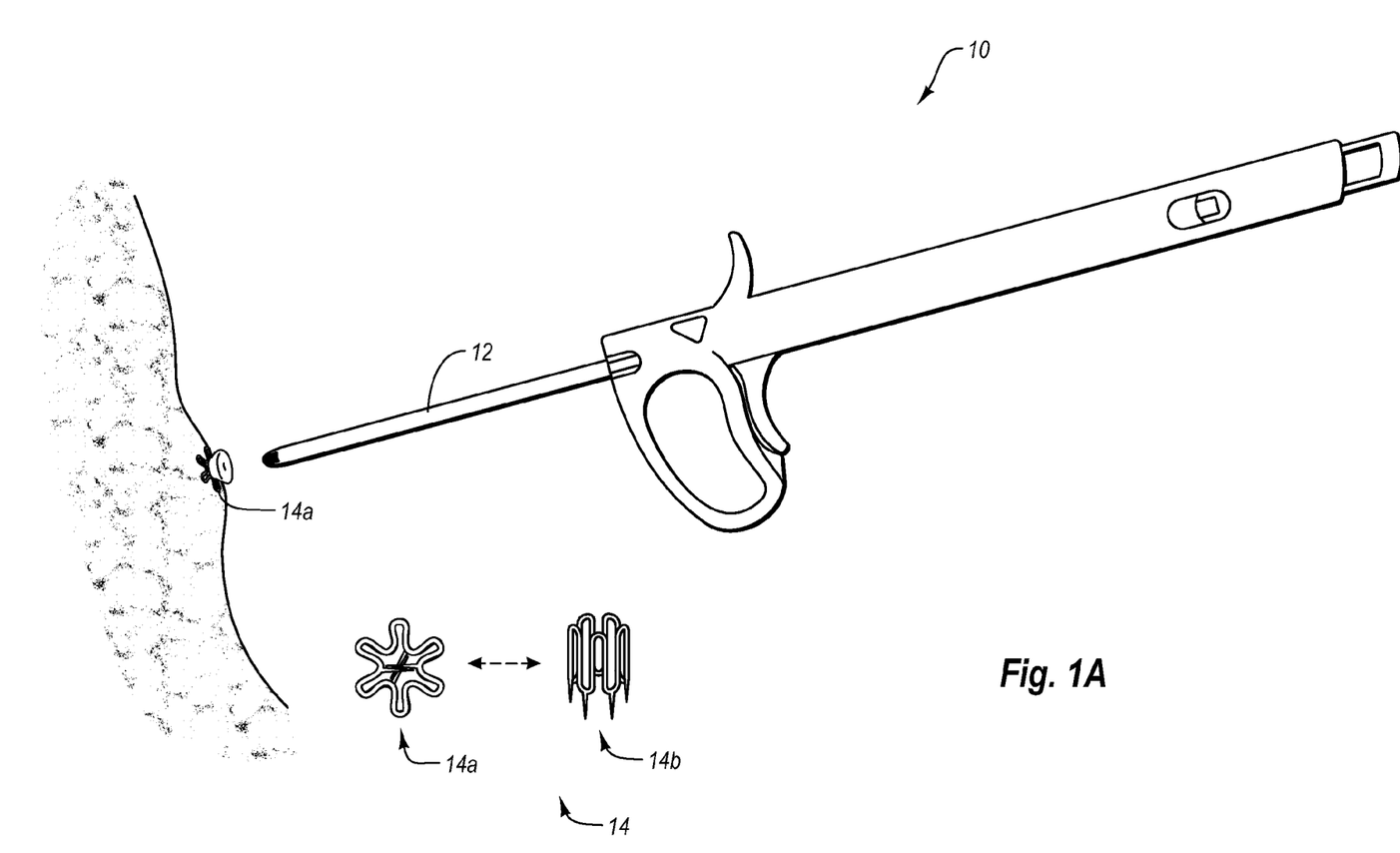
FIG. 1A illustrates a delivery device, a closure element in both compressed and relaxed conformations, and a schematic in which the closure element is delivered to a tissue opening.

For example, FIG. 1A illustrates a delivery device 10 in accordance with an implementation of the present invention, as it has been used to deliver a closure element or clip 14(*a-b*) onto a tissue surface. FIG. 1A shows the configuration of delivery device 10 following deployment of the clip or closure element 14. When delivered, FIG. 1A shows that closure element 14 closes about the tissue in a relaxed conformation 14*a*, pinching the tissue closed.

In addition, FIG. 1A shows that closure element 14 can be found in at least one of two different conformations: relaxed 14*a* and tensioned 14*b*. One will appreciate, however, that the number or type of various states possible for a given closure element 14 can depend on the type of material used to create the closure element 14 in the first instance. In one implementation, for example, closure element 14(*a-b*) comprises a shape memory material, such as a shape memory plastic, shape memory polymer, or shape memory metal or alloy. In one configuration, the shape memory alloy is NITINOL, or an alloy composite thereof. In additional or alternative implementations, however, closure element 14 comprises any other number of resiliently deformable materials, including natural or synthetic rubber or plastic materials, or metallic combinations thereof. These other materials, or other forms of designs, may alternatively employ different variations on the shape or conformation of the illustrated tension/relaxed states 14*a-b*, and/or different degrees of tension forces.

Figure 1B:
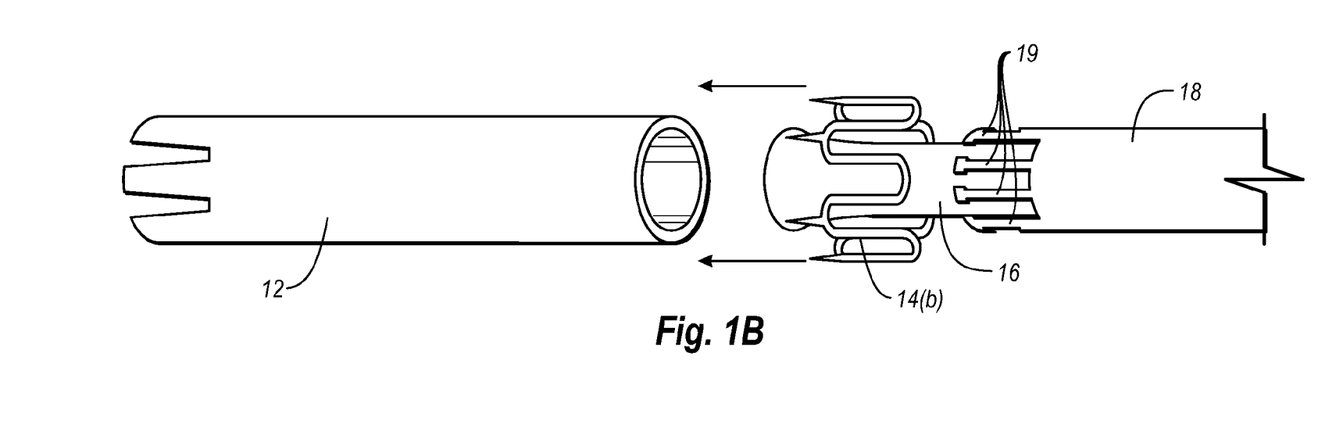
FIG. 1B illustrates a closure element and pusher tube positioned about a carrier tube prior to insertion into a garage tube.
Figure 1C:
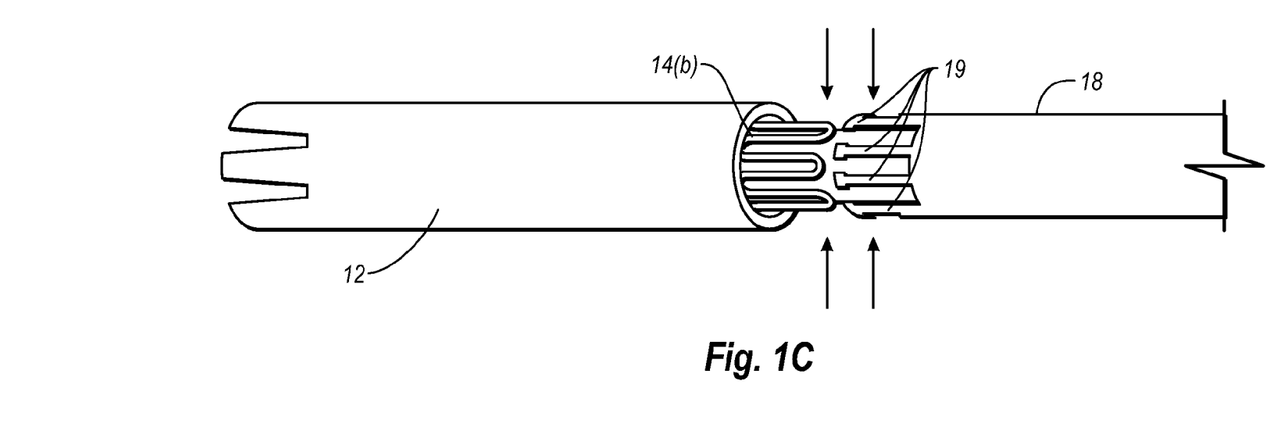
FIG. 1C illustrates the components of FIG. 1A in which the closure element and the flanges of the pusher tube are compressed prior to or during insertion into the garage tube.

In the present case, FIG. 1A shows that closure element 14 can alternate between a planar configuration (relaxed state 14*a*) and a non-planar configuration (tensioned state 14*b*). In the relaxed, or planar configuration 14*a*, the closure element is in a shape suitable for pinching tissue to close a puncture in a vessel. By contrast, the tensioned state 14*b* of the closure element is a columnar formation that is generally better suited for insertion or storage within the delivery device 10, such as in garage tube 12. Despite this columnar formation in the tensioned state 14*b*, however, closure element 14 may need still further compaction. As shown in FIG. 1B, for example, the tensioned form 14*b* of the closure element may still extend somewhat outside of a circumference defined by the garage tube 12 cross-section. Similarly, FIG. 1B shows that the flanges 19 of pusher tube 18 may also extend outside of this circumference. Further, the end of carrier tube 10 that supports the closure element 14 can also be extended outside of this circumference.

Figures 2A, 2B:
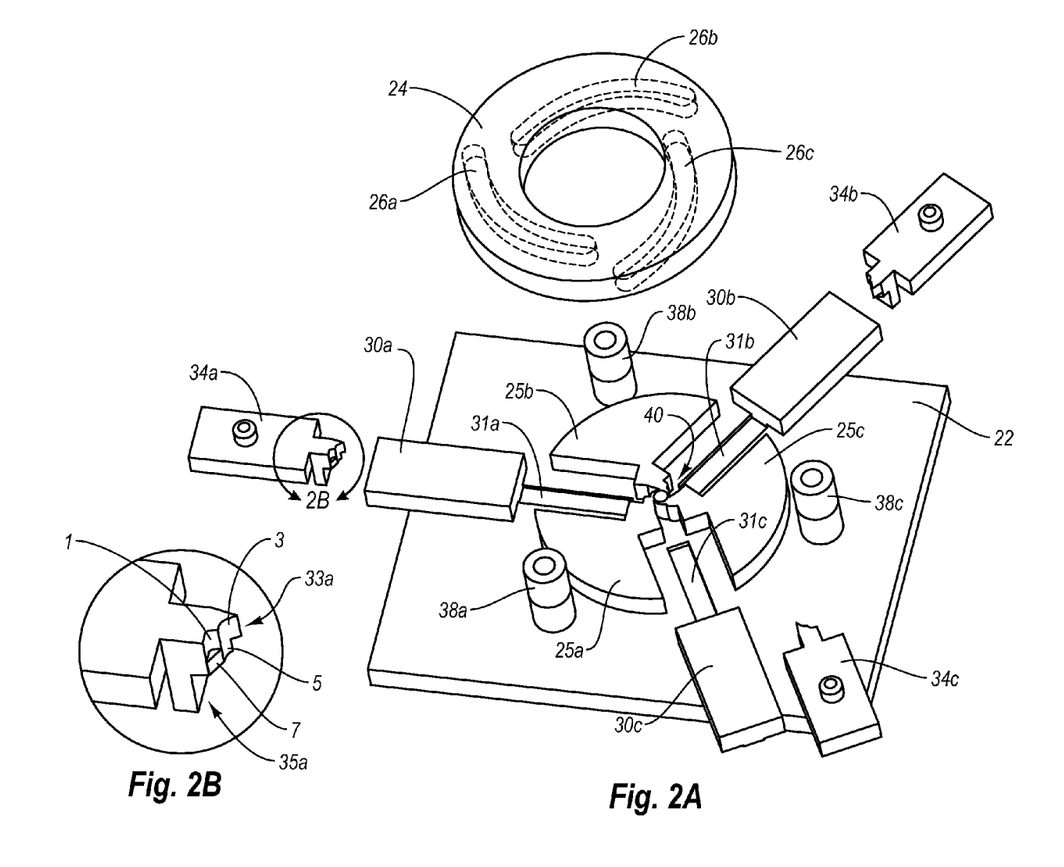
FIG. 2A illustrates an exploded view of one or more components of a compression tool that can be used in accordance with an implementation of the present invention.
FIG. 2B illustrates a close up perspective view of a front end of a cam-actuated clamp.

Accordingly, FIG. 2A illustrates a compression tool 20 in exploded view. In particular, FIG. 2A illustrates a number of the components that can be used to compress each of the above-described delivery device components (e.g., 14, 16, etc.), and in particular to any degree necessary for insertion in garage tube 12. In general, and as will be understood more fully herein, compression tool 20 can include (i) a base; (ii) actuation means; (iii) clamping means; and (iv) receiving means. With respect to FIG. 2A, at least one implementation of a base comprises support surface 22. This support surface 22 can form part of a table, bench, or structure that can support the compression tool 20 during use. Alternatively, the support surface 22 can be a support structure that appends with or to a table, bench or other station that supports the support surface 12 during use.

In addition, FIG. 2A shows that at least one implementation of actuation means can comprise at least one rotating member 24, rotation supports 25a, 25b, and 25c, as well as roller posts 38a, 38b, and 38c. Furthermore, FIG. 2A shows that at least one implementation of clamping means can comprise a plurality of clamps 34a-c mounted on corresponding blocks 30a-c. Still further, FIG. 2A shows that at least one implementation of receiving means includes a center point 40, which includes at least a hollow portion of support surface 22 surrounded by rotation supports 25a-c (compare FIG. 2A with FIGS. 4A-4B).

As will be understood more fully herein, a user can rotate the actuation means when each component of a delivery device assembly is in appropriate position, such as in receiving means, or in a cavity/center point of the support surface. Rotating the actuation means, in turn, actuates the clamping means, which compresses the delivery device components with a differentially shaped proximal end. For example, FIG. 2B (see also FIGS. 4A-4B) shows that the proximal end of clamp 34a can include a first contact point 33a having differential surfaces 1, 3, 5, and 7, as well as a second contact point 35a. In general, second contact point 35a is recessed from first contact point 33a, and is configured to extend downward into a support surface recess, such as recess 31a. In one implementation, this extension of point 35a into recess 31a acts to help guide clamp 34a and block 30a along recess 31a.

In addition, and as will be understood more fully in FIGS. 3A-4B, the differential surfaces 1, 3, 5, and 7 of contact point 33a can enable a variety of different functions for compressing the closure element 14. For example, FIG. 2B shows that surfaces 3 and 5 provide a contact interface against closure element 14, and are also offset. As a result of this offset, only surface 3 directly contacts the closure element 14 in the closed position. Moreover, because surface 5 of contact point 33a is recessed, surface 5 provides space for receiving garage tube 12 when each of clamps 30a-c are in a closed position.

By contrast, FIG. 2B shows that surfaces 1 and 7, which may not directly contact closure element 14, can also include differential spacing, formations, or other forms of shaping. In one implementation, for example, surfaces 1 and 7 of contact point 33a are specifically shaped to accommodate the proximal ends of an adjacent or opposed clamp, particularly which those clamps are in the closed position. Thus, and will be shown more fully with respect to FIGS. 3A-3B, when the clamps are in a closed position, at least one surface is configured or shaped to compress closure element 14, another surface is configured to provide an entry point for garage tube 12, and still another surface of contact point 33a is configured to accommodate potentially abutting surfaces of other clamps.

Figure 3A:
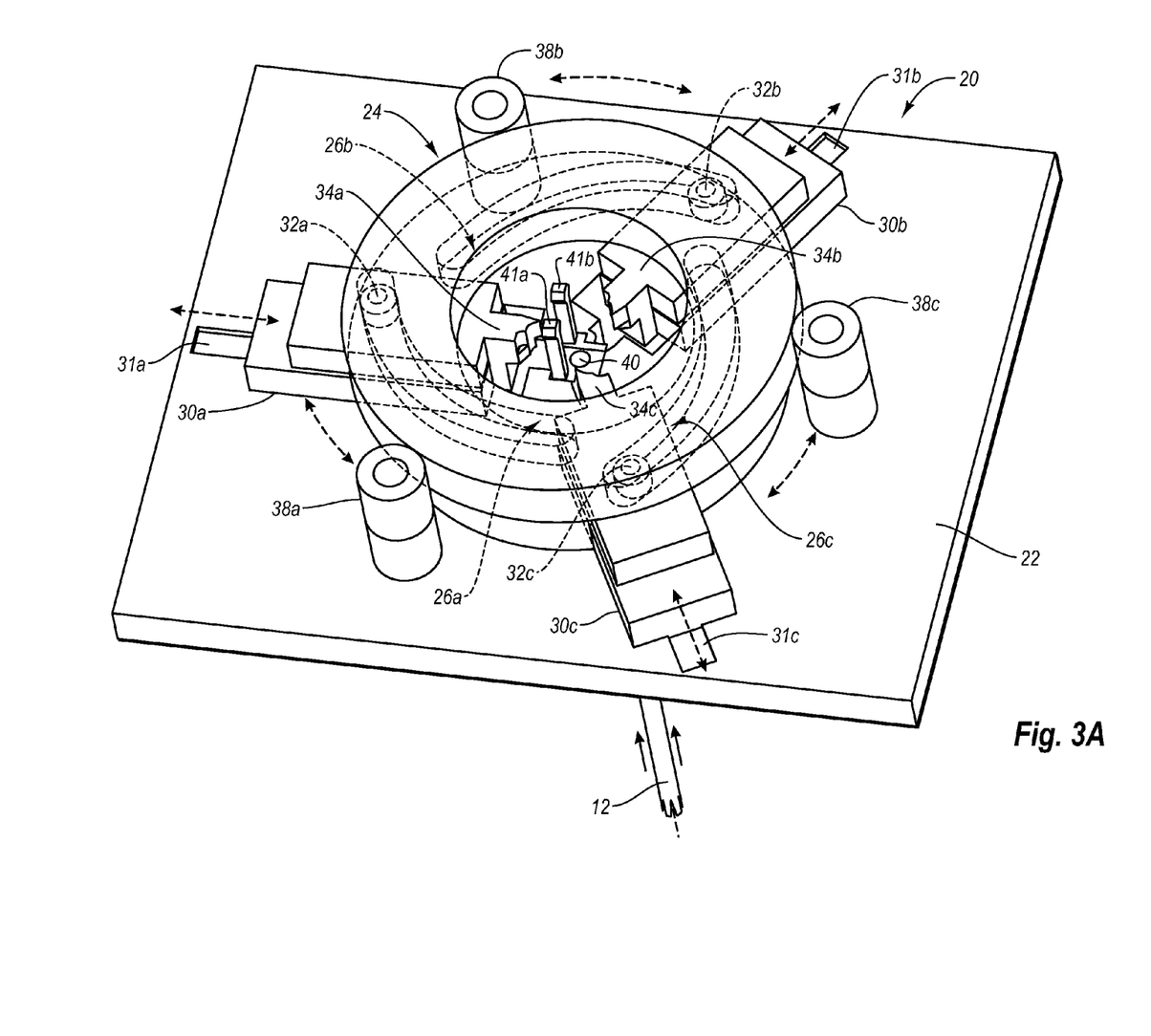
FIG. 3A illustrates the compression tool of FIG. 2A in assembled form, further showing cam-actuated clamps in an open position.
Figure 3B:
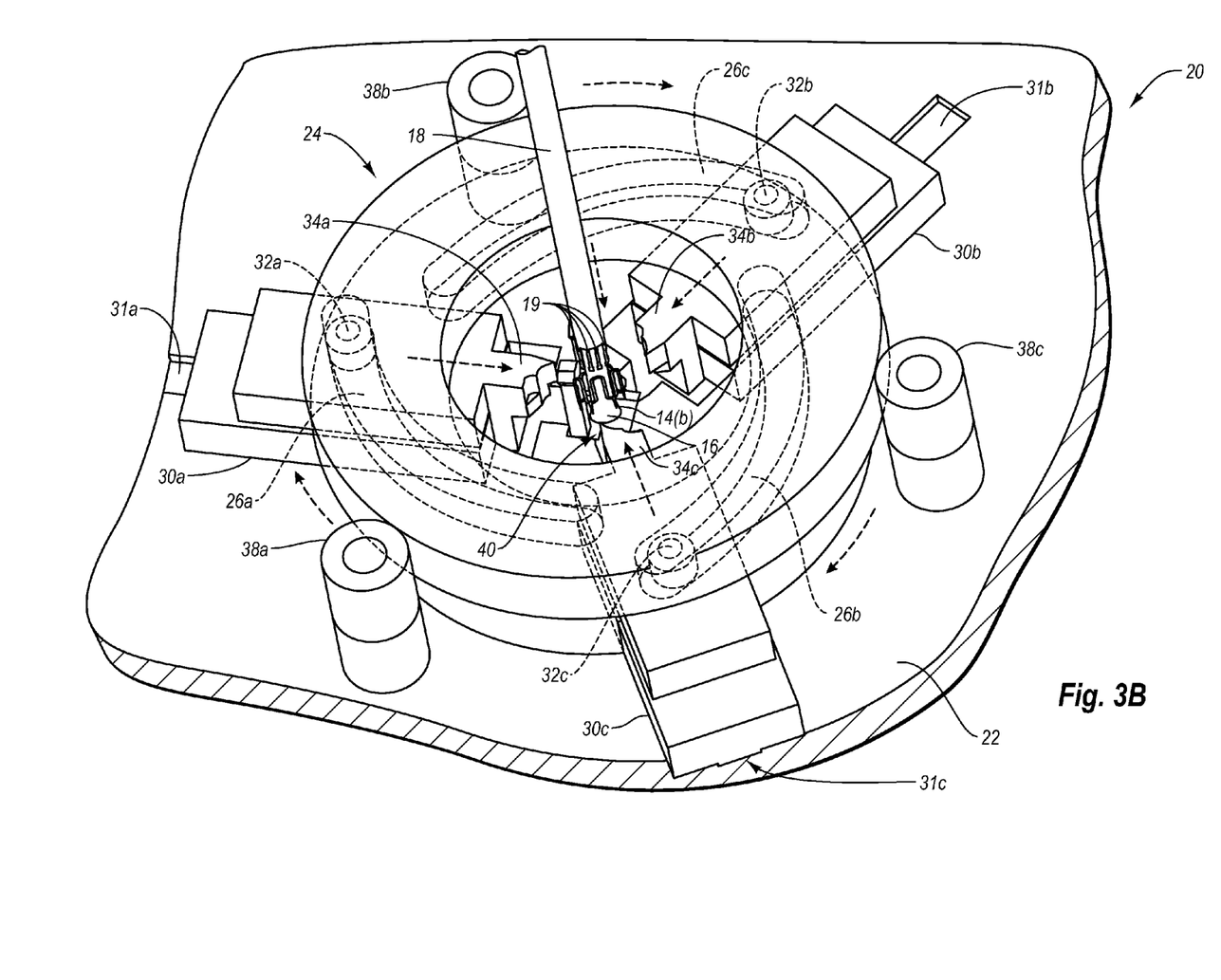
FIG. 3B illustrates the compression tool and apparatus of FIG. 3A, wherein the carrier tube, closure element, and pusher tube components are in a position to be compressed.
Figure 3C:
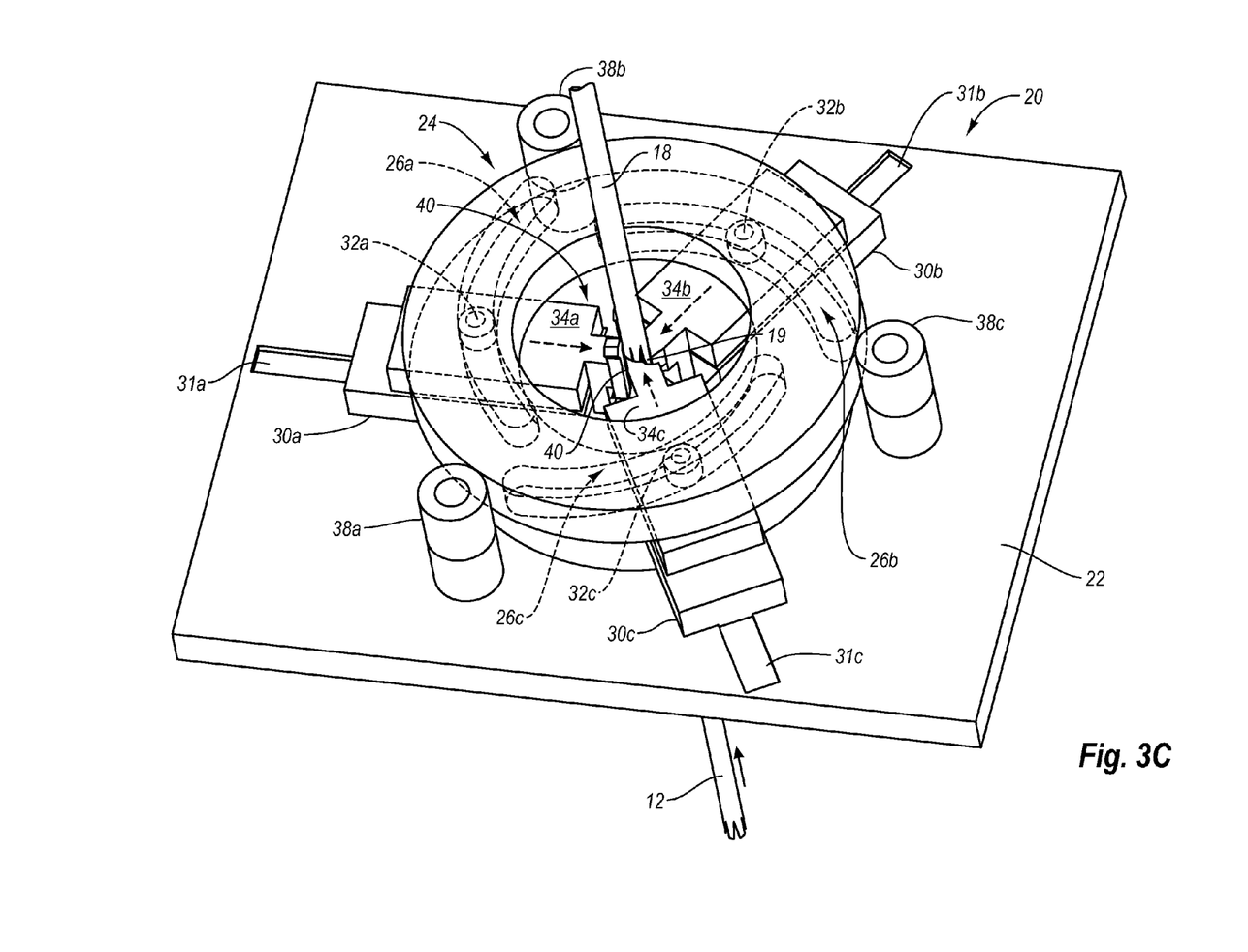
FIG. 3C illustrates the compression tool and apparatus of FIG. 2B, where the plurality of cam-actuated clamps are closed about the carrier tube, closure element, and pusher tube.

FIGS. 3A-3C illustrate at least one implementation of the above-described mechanisms or components, and, in particular, how these mechanisms/components can operate in concert to engage or disengage the clamps. As shown in FIG. 3A, for example, engagement can be accomplished at least in part using rotating member 24. In general, rotating member 24 can include a generally disc-shaped apparatus, though other shapes or styles may be appropriate in other operating environments or implementations. In addition, FIG. 3A illustrates a plurality of supports 41a and b, which can be used to help stabilize the device 10 assembly components prior to installation. Furthermore, FIG. 3A shows the plurality of roller posts 38a-c mounted on support 22, and further positioned along tangential points of rotating member 24. In at least one implementation, the plurality of roller posts 38a-c are configured to maintain the position (and facilitate the rotation) of rotating member 24 through a plurality of rotation degrees.

In addition, and to actuate the clamping means, FIG. 3A shows that the actuation means further comprises a series of grooves 26a-c formed inside rotating member 24. In particular, FIG. 3A shows that grooves 26a-c are formed in a progressive or regressive radial direction within rotating member 24, so that the grooves 26a-c are directed in a progressively or regressively radial direction toward or away from the center of rotating member 24, depending on the direction by which rotating member 24 is rotated. These radially directed grooves 26a-c are configured to guide one or more cam elements (32a, 32b, 32c) along the groove 26a, 26b, or 26c length, and correspondingly direct clamping means in a linear direction essentially perpendicular to the direction by which rotating member 24 is rotated.

For example, FIG. 3A shows that at least one corresponding cam element 32a, 32b, or 32c is mounted on the body of corresponding clamps 34a-c, and is positioned within one of grooves 26a, 26b, or 26c of the rotating member 24. As the grooves rotate in either a clockwise or counterclockwise direction, the cam elements 32a-c are configured to slide, glide, rotate, or otherwise move along a path defined by grooves 26a-c. Nevertheless, cam elements 32a-c are configured to remain in a substantially fixed position relative to a given portion. As previously mentioned, FIG. 3A shows that each cam element 32a, 32b, or 32c, is fixedly attached to a particular clamp 34a, 34b, or 34c of the clamping means. The clamping means, in turn, are configured to slide radially outward or inward with respect to the receiving means. In particular, movement of the cam elements 32a-c within grooves 26a-c causes the clamping means to move radially inward or outward with respect to the receiving means.

For example, FIG. 3A shows that each of the plurality of clamps 34a-c is mounted on corresponding blocks 30a, 30b, or 30c of the clamping means. The plurality of blocks 30a-c, in turn, can be mounted in a substantially fixed position with respect to the clamps 34a-c on one side, and slidably mounted to the support surface 22. In one implementation, blocks 30a-c each comprise one or more tracks or other extension members configured to glide within a corresponding recess 31a, 31b, or 31c. In additional or alternative configurations, however, the plurality of blocks are fixedly mounted to the support surface 22, and the clamps 34a-c are slidably mounted to the plurality of blocks 30a-c. In still further alternative implementations, the plurality of clamps may be mounted on an upper side of support surface, with the blocks being mounted underneath the support surface (e.g., the side on which the garage tube 12 is received).

In either case, grooves 26a-c of actuation means, as well as blocks 30a-c, cam elements 32a-c, and clamps 34a-c of the clamping means are configured to operate in concert to translate rotation of rotation member 24 into linear clamping motion. In particular, each of these components work together to linearly-slide clamps 34a-c with rotation of rotating member 24, and move clamps 34a-c along the radius of rotation member 24, or in a direction linearly toward or from the receiving means. In this particular illustration of FIG. 3A, for example, clockwise rotation of rotating member 24 causes clamps 34a-c to close inward toward the receiving means (center point 40) of device 20, while counterclockwise rotation causes clamps 34a-c to open away from the receiving means.

For example, FIG. 3B illustrates compression tool 20 as a user rotates rotating member 24 during the initial stages of device 10 assembly. At the outset and prior to rotation, FIG. 3B shows that the user has prepared a preliminary device assembly, which includes the closure element 14 in a tensioned state 14b about carrier tube 16, and adjacent flanges 19 of pusher tube 18. The user has also positioned this preliminary assembly in the receiving means portion (e.g., center point 40) of support surface 22. FIG. 3B shows that, once in appropriate position, the user then initiates rotation of the rotation member 24 in the clockwise direction. In the illustrated case, therefore, this clockwise rotation causes the plurality of clamps 34a-c to move toward the receiving means portion, or toward center point 40.

FIG. 3C thus illustrates compression tool 20 in a closed state, or after a user has rotated the actuation means, to clamp the preliminary assembly. For example, FIG. 3C shows that clamps 34a-c are completely pressed against flanges 19 (partially hidden), and further pressed against closure element 14 (hidden). In this closed or compressed state for the preliminary assembly, the user can then apply garage tube 12 from an underneath position through center point 40, and thus about closure element 14 and flanges 19.

Figure 4A:
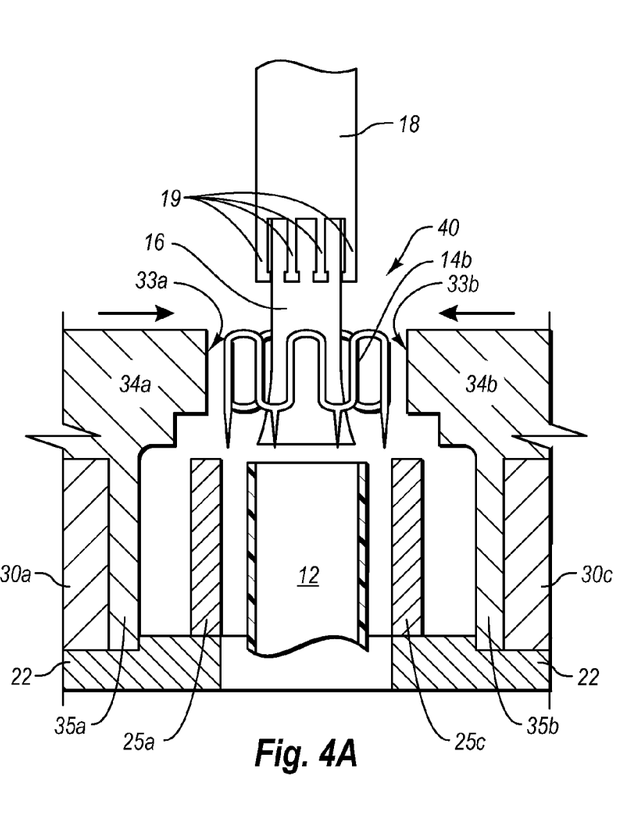
FIG. 4A illustrates a schematic cross-sectional diagram of the carrier tube, pusher tube, closure element, and garage tube from a side view when in the position shown in FIG. 3B.
Figure 4B:
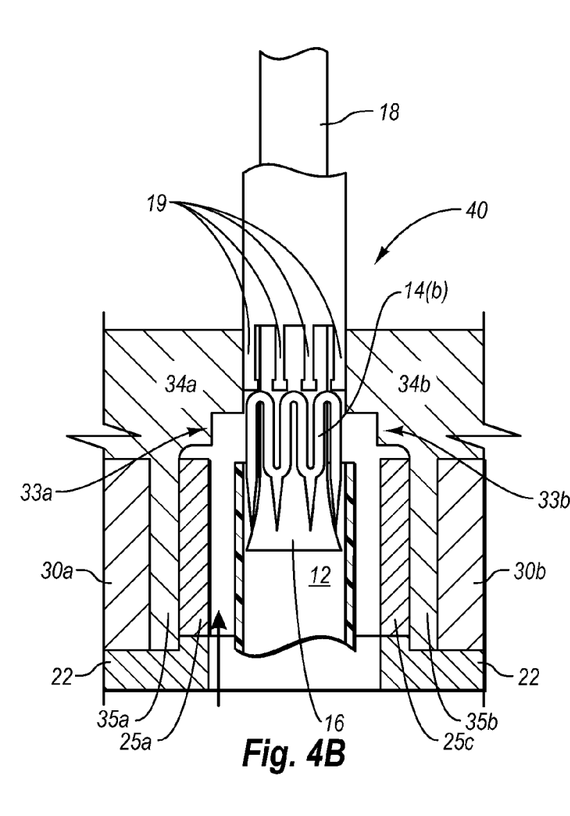
FIG. 4B illustrates a schematic cross-sectional diagram of the carrier tube, pusher tube, closure element, and garage tube from a side view when in the position shown in FIG. 3C.

FIGS. 4A and 4B provide a schematic diagram regarding the positioning of the preliminary assembly during closing of the clamping means. In particular, FIG. 4A shows that each clamp 34a-c of the clamping means comprises a specially formed contact portion 33a/35a and 33b/35b. In the illustrated implementation, the contact portion is differentially shaped (portion 33a compared with 35a, etc.), and approximately "L-shaped" in the illustrated case. As shown, the contact portion 33a/b of each of the clamps 34a-c is configured to enable the preliminary assembly of device 10 to be compressed at one point (e.g., 33a-b), but nevertheless allow sufficient room or gapping (e.g., 35a-b) to abut a portion of the receiving means 25a, 25c.

Accordingly, FIG. 4A illustrates a schematic of the preliminary assembly as it might appear at the point in time illustrated in FIG. 3A or 3B, while FIG. 4B illustrates a schematic of the preliminary assembly as it might appear at the point in time illustrated in FIG. 3C. In particular, FIG. 4B shows that clamps 34a-b are sufficiently closed, such that portions 33a-b of their corresponding contact portions have compressed closure element 14 and flanges 19. By contrast, FIG. 4B also shows that portions 35a-b of clamps 34a-b are positioned against the terminal ends of rotation supports 25a and 25c. As such, garage tube can be inserted up through this gap, and about the compressed closure element 14, carrier tube 16, and flanges 19 to complete the assembly of delivery device 10.

Figure 5:
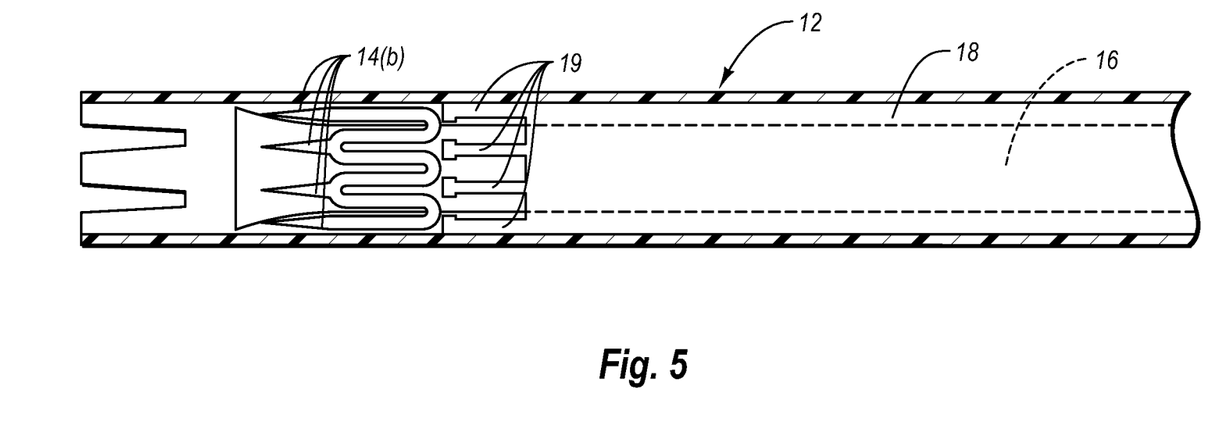
FIG. 5 illustrates an assembled delivery device after the carrier tube, closure element, and pusher tube have been compressed and/or otherwise assembled into the garage tube.

Upon assembly of device 10, or in the least, assembly of garage tube 12 about closure element 14, carrier tube 16, and pusher tube 18, the user can then release the components by releasing actuation means. To do so, the user can simply reverse the rotation of the actuation means, such as by turning rotating member 24 in a reverse direction as before. Due at least in part to the combined cam action of grooves 26a-c with cam elements 32a-c, the reverse rotation causes the clamping means to retreat from the receiving means (e.g., move away from center point 40). Upon removing the components from compression tool 20, the user can then slide garage tube 12 over the remainder of the device assembly, as needed. Along these lines, FIG. 5 illustrates a schematic of a terminal end of a delivery device that has been assembled in accordance with the components and principles previously described.

Accordingly, FIGS. 1A through 5 and the corresponding text provide a number of different schematics and components for efficiently assembling a closure element (e.g., for closing tissue) within a medical delivery device. In particular, the systems, apparatus, and components described herein allow a user to much more efficiently assemble components that need to be compressed and inserted into a particular delivery device. As previously mentioned, however, one will appreciate that the systems, apparatus, components and corresponding concepts can be applied in a wide range of settings and to a wide range of devices that carry compressed or tensioned components. Furthermore, the apparatus, components, and general concepts are not limited to any particular type or form of material, so long as the actuation means, clamping means, and receiving means are generally configured to operate as described herein.

The present invention may thus be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes that come within the meaning and range of equivalency of the claims are to be embraced within their scope.

I claim:

1. A compression tool configured to compress a closure element of a preliminary assembly of a medical delivery device, the compression tool comprising:

a base configured with a receiving means, the receiving means being configured to receive the closure element of the preliminary assembly of the medical delivery device on a first side, and on a second side to receive a garage tube that is sized and configured to accommodate insertion of the closure element in a compressed configuration;

a clamping means positioned about the receiving means, the clamping means including a clamp being configured to slide radially in a linear direction toward or away from the receiving means, the clamp including a differentially shaped contact portion having a first portion that includes a first surface sized and configured to clamp against the closure element and a second surface sized and configured to accommodate insertion of the garage tube, the second surface being recessed radially relative to the first surface;

an actuation means configured to, upon application of force in one direction, rotate about a rotation axis in a first direction relative to the base, thereby sliding the clamp of the clamping means radially in a linear direction toward the receiving means, and upon application of force in an opposite direction, rotate in a second direction, opposite to the first direction, relative to the base thereby sliding the clamping means away from the receiving means; and wherein the clamp of the clamping means is configured to remain stationary in longitudinal direction along the rotation axis as the clamp slides in the linear direction toward the receiving means.

2. The compression tool as recited in claim 1, wherein the receiving means comprises a hollow center point formed within a support surface of the base.

3. The compression tool as recited in claim 1, wherein the clamping means comprises a plurality of clamps slidably positioned about the receiving means.

4. The compression tool as recited in claim 1, wherein the clamping means further comprise a plurality of cam elements mounted thereon.

5. The compression tool as recited in claim 4, wherein:
the actuation means comprises a rotation member having a plurality of radially-formed grooves; and
each of the plurality of grooves is configured to fit about one of the plurality of cam elements.

6. The compression tool as recited in claim 5, wherein the actuation means are configured to move the plurality of cam elements within the plurality of radially-formed grooves in response to clockwise or counterclockwise rotation of the actuation means.

7. The compression tool as recited in claim 1, wherein:
the actuation means includes a rotating member engaged with the clamping means; and
the base comprises a rotation support supporting the rotating member.

8. The compression tool as recited in claim 7, wherein the rotation support includes an opening sized and configured to accommodate the garage tube therein.

9. A compression tool configured to compress one or more components of a preliminary assembly of a medical delivery device, the compression tool comprising:
a base having a support surface and a hollow center point, the hollow center point being configured to receive an unassembled portion of a delivery device on one side, and on another side to receive a preliminary assembly of components to be inserted;
a plurality of clamps slidably positioned about the hollow center point, each of the plurality of clamps including a differentially shaped contact portion having a first portion that includes a first surface sized and configured to clamp against the preliminary assembly and a second surface recessed radially relative to the first surface;
a plurality of cam elements coupled to the plurality of clamps;
a rotating member rotatably coupled to the plurality of cam elements, upon rotation about a rotation axis, the rotating member being configured to cause each of the plurality of clamps to radially slide in a linear direction toward the hollow center point or away from the hollow center point; and
wherein the plurality of clamps are configured to remain stationary in a lateral direction along the rotation axis, relative to the base, to the rotating member, and to the rotation axis as the plurality of clamps slide in the linear direction toward the hollow center point or away from the hollow center point.

10. The compression tool as recited in claim 9, further comprising a plurality of rotatable posts mounted to the support surface, wherein one or more rotatable posts of the plurality of rotatable posts are in contact with the rotating member along a perimeter thereof, the rotatable posts being configured to stabilize the rotating member during rotation.

11. The compression tool as recited in claim 9, wherein:
the rotating member has a plurality of radially formed grooves, each of the plurality of radially formed grooves having a progressive or regressive radial direction; and
each cam element of the plurality of cam elements is configured to fit within a corresponding axially formed groove of the plurality of axially formed grooves.

12. The compression tool as recited in claim 11, wherein each axially formed groove of the plurality of axially formed grooves graduates in the same radial direction relative to a center point of the rotating member.

13. The compression tool as recited in claim 12, wherein the grooves and the plurality of cam elements are configured to cooperate to cause each of the plurality of clamps to radially slide in a linear direction toward the hollow center point or away from the hollow center point.

14. The compression tool as recited in claim 11, wherein the rotating member is substantially circular.

15. The compression tool as recited in claim 11, further comprising a plurality of blocks coupled to the plurality of clamps.

16. The compression tool as recited in claim 11, wherein the base further comprises a plurality of recesses configured to guide the plurality of clamps in a linear direction toward the hollow center point and away from the hollow center point.

17. The compression tool as recited in claim 16, further comprising a plurality of blocks coupled to the plurality of clamps, a portion of each block of the plurality of blocks extending into corresponding recesses in the base.

18. The compression tool as recited in claim 9, wherein each clamp of the plurality of clamps comprises a differentially formed contact portion, the contact portion being configured to compress one or more internal components of a delivery device on one portion and to abut a terminal portion of a rotation support.

\* \* \* \* \*